US00PP34053P2

(12) United States Plant Patent
Hansen

(10) Patent No.: US PP34,053 P2
(45) Date of Patent: Mar. 22, 2022

(54) ***LEUCANTHEMUM* PLANT NAMED 'ICE CREAM DREAM'**

(50) Latin Name: ***Leucanthemum* x *superbum* (Bergmans ex J.W.Ingram) D.H.Kent**
Varietal Denomination: Ice Cream Dream

(71) Applicant: Hans A Hansen, Zeeland, MI (US)

(72) Inventor: Hans A Hansen, Zeeland, MI (US)

(73) Assignee: Walters Gardens Inc., Zeeland, MI (US)

( * ) Notice: Subject to any disclaimer, the term of this patent is extended or adjusted under 35 U.S.C. 154(b) by 0 days.

(21) Appl. No.: 17/300,224

(22) Filed: Apr. 16, 2021

(51) Int. Cl.
*A01H 5/02* (2018.01)
*A01H 6/14* (2018.01)

(52) U.S. Cl.
USPC ..... Plt./285

(58) Field of Classification Search
USPC ..... Plt./285
CPC ..... A01H 5/02; A01H 5/00; A01H 6/14
See application file for complete search history.

*Primary Examiner* — June Hwu

(57) ABSTRACT

The new Shasta daisy plant, *Leucanthemum* 'Ice Cream Dream', is a sturdy plant with green serrated foliage and stiff stems. The numerous freely-flowering inflorescences producing buds beginning with intense yellow ray florets developing to near white in the perimeter. The outer ray florets are lanceolate to linear and emarginate to cleft and the inner ray florets are mostly cleft and retain their yellow coloration longer. The center disk florets are yellow. Flowering repeats into fall if deadheaded. The new plant is useful in the landscape as a long-flowering border, in mass, as accent plants and containerized for patio or indoor use, or as a cut flower.

1 Drawing Sheet

Botanical classification: *Leucanthemum* x *superbum* (Bergmans ex J. W. Ingram) D. H. Kent.
Variety denomination: 'Ice Cream Dream'.

STATEMENT REGARDING PRIOR DISCLOSURES UNDER 37 CFR 1.77(b)(6)

The first non-enabling disclosure of the claimed plant was made by Walters Gardens, Inc. on Feb. 1, 2020 in the form of a website brief description and photograph followed by a short description and photograph in the "Walters Gardens 20-21 Catalog" by Walters Gardens, Inc. The first enabling disclosure of a sales of the claimed plant was on Jun. 29, 2020 by Walters Gardens, Inc. Walters Gardens, Inc. obtained the new plant and information about the new plant directly from the inventor. No plants of *Leucanthemum* 'Ice Cream Dream' have been sold, in this country or anywhere in the world, nor has any disclosure of the new plant been made, more than one year prior to the filing date of this application, and such sale or disclosure within one year was either derived directly or indirectly from the inventor.

BACKGROUND OF THE INVENTION

The original *Leucanthemum* x *superbum*, or Shasta daisies, were bred by Luther Burbank in the late 1800's as a cross between *Leucanthemum maximum* (Ramond) DC. with *Leucanthemum vulgare* (Vaill.) Lam., *Leucanthemum lacustre* (Broth.) Samp. and *Nipponanthemum nipponicum*. The new plant, *Leucanthemum* 'Ice Cream Dream' originated from a planned breeding program of the inventor at a wholesale perennial nursery in Zeeland, Mich., USA. The new *Leucanthemum* was a single plant selected from a group of seedlings from a self-pollination on Jul. 16, 2014 of 'Sante' U.S. Plant Pat. No. 19,829. The individual plant that eventually became 'Ice Cream Dream' was first evaluated in the summer of 2015 and originally given the breeder number 14-26-04 through the subsequent evaluations.

The present invention relates to a new and distinct cultivar of Shasta daisy botanically known as *Leucanthemum* x *superbum* and hereinafter referred to by the cultivar name 'Ice Cream Dream' or the new plant.

Asexual reproduction of the new cultivar by basal cuttings and shoot tip tissue culture at the same nursery in Zeeland, Mich. as early as the summer of 2016 has demonstrated that the new cultivar reproduces true to type with all of the characteristics of the original plant retained through successive generations of asexual propagation.

BRIEF SUMMARY OF THE INVENTION

The new plant, *Leucanthemum* 'Ice Cream Dream', is most closely compared to *Leucanthemum* 'Sante' and 'Banana Cream' U.S. Plant Pat. No. 23,181 in flower and *Leucanthemum* and 'Cream Puff' U.S. Plant Pat. No. 30,074, 'Snowcap' (not patented) and 'Whoops-a-Daisy' U.S. Plant Pat. No. 27,259 in compact habit. In test trials in Zeeland, Mich., 'Cream Puff' has a slightly taller habit and has flowers that are less double and the ray floret ligules are less dissected. 'Banana Cream' is slightly taller in habit, the ligules are slightly less yellowish, and the inflorescence has more ray florets. Compared with 'Whoops-a-Daisy' and 'Snowcap' the new plant is slightly smaller in habit and the ray floret ligules of 'Ice Cream Dream' are more numerous, have more yellowish coloration and are more dissected. Compared with 'Sante', the inflorescence of 'Ice Cream Dream' are larger, with more ray florets of a more yellowish coloration and the habit is shorter with flowers from the top of the plant down to the soil.

*Leucanthemum* 'Ice Cream Dream' differs from all cultivars known to the inventor in the following combined traits:

1. Sturdy, compact, dense, mounded plants with green serrated foliage and stiff stems;
2. Inflorescence of numerous semi-double capitulum.
3. Outer rows of ray florets with ligules lanceolate to linear and emarginate to cleft;
4. Inner rows of ray florets with ligules tending to be more cleft;
5. Center disk florets of yellow;
6. Ray floret ligules beginning intense yellow with outer ligules lightening to near white;
7. Freely flowering habit and repeating if deadheaded.

BRIEF DESCRIPTION OF THE PHOTOGRAPHS

The photographs of 'Ice Cream Dream' demonstrate the overall appearance and landscape qualities of the new plant, including the unique traits planted in a full-sun trial garden in Zeeland, Mich. The colors are as accurate as reasonably possible with color reproductions. Ambient light spectrum, source, direction and temperature may cause the appearance of minor variation in color.

DETAILED BOTANICAL DESCRIPTION

Figure 1:
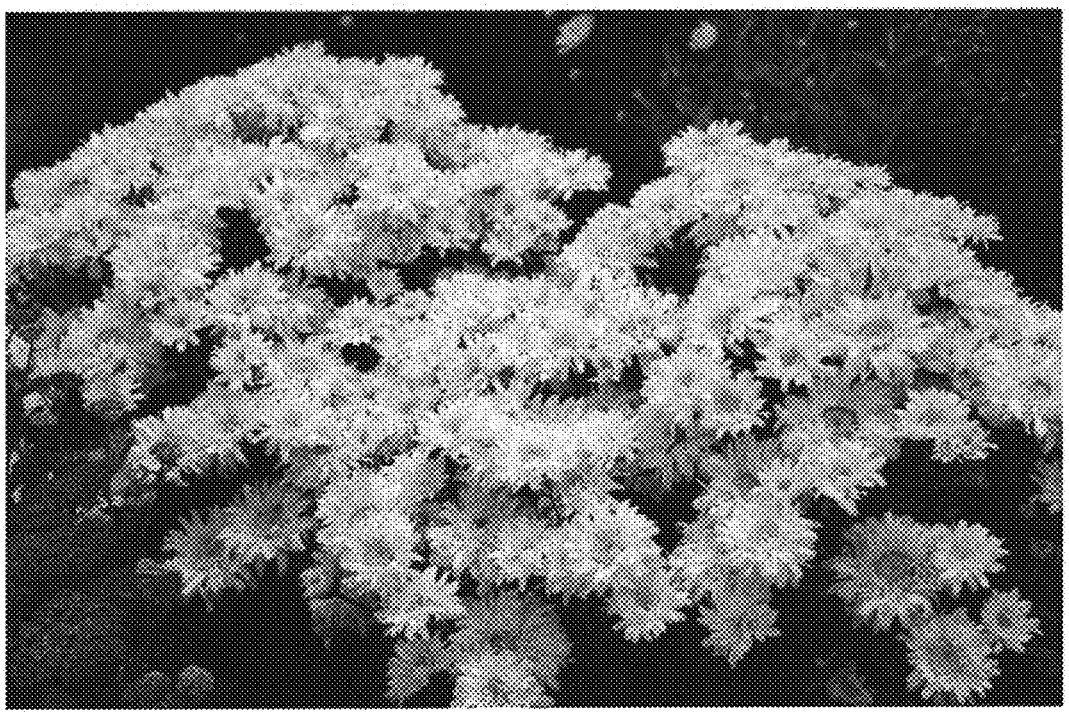
FIG. 1 Shows a two-year-old new plant at peak flowering with inflorescences covering the plant from nearly top to ground.
Figure 2:
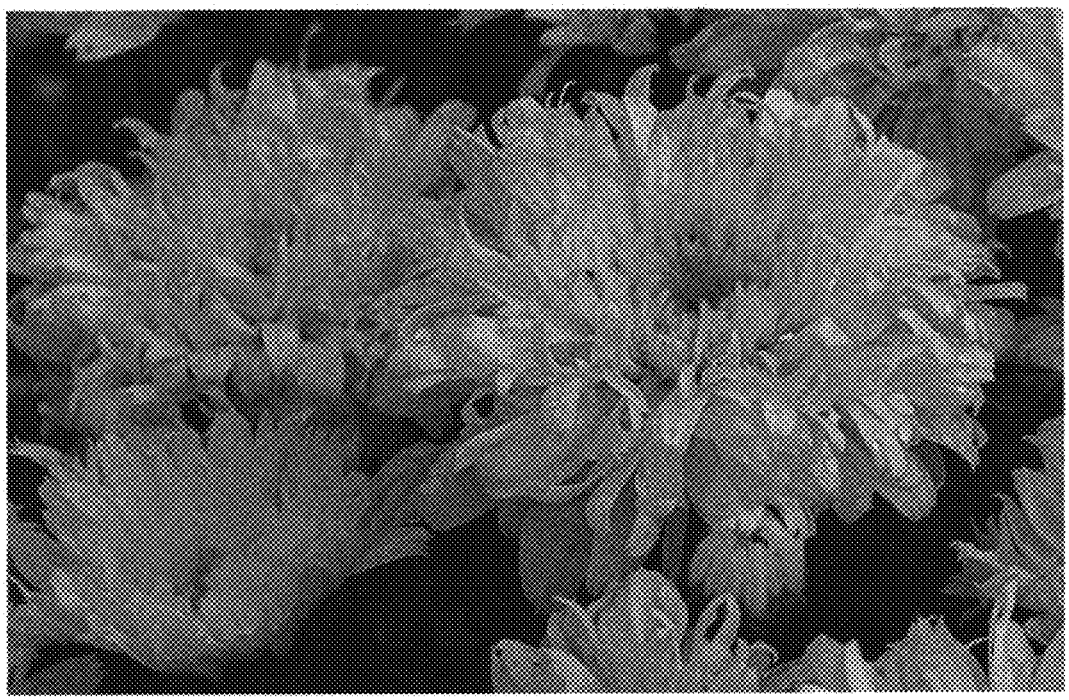
FIG. 2 Shows a close-up of the inflorescence and the buds.

The following descriptions and color references are based on the 2015 edition of The Royal Horticultural Society Colour Chart except where common dictionary terms are used. The new plant has not been observed in all possible environments and conditions. The phenotype of *Leucanthemum* 'Ice Cream Dream' may vary with different growing conditions such as changes in temperature, light intensity, water availability, fertility, but without change in the genotype.

The plants used for description purposes were two years old and were grown in Zeeland, Mich. in a full-sun, loamy-sand trial plot environment with supplemental water and limited fertilizer as needed. Summer temperatures range from night lows of about 10° C. to daytime highs of about 34° C. Measurements and numerical values represent averages of trial plants.

Botanical classification: *Leucanthemum* x *superbum;*

Parentage: The female and male parents are both 'Sante';

Habit: Herbaceous perennial with about 45 branched stems arising from rhizome base; each stem having three to six inflorescences each, rarely two; about 30 cm tall and 42 cm across with rounded top and sides; flowering from top to nearly soil level;

Roots: Fibrous, thin, heavily branched; root color nearest RHS 155D depending on soil type;

Propagation: Tip cuttings or tissue culture; about two weeks to produce roots from cutting; about 33 weeks to finish to flower in 3.8 liter pot depending on season;

Stems: About forty-five main stems per plant; strong; mostly upright; canaliculated; sparsely hispidulous; terete, hollow in distal portion; 10.0 mm diameter at base; to 28 cm tall; about 13 nodes before flowers; average internode length about 1.0 cm;

Stem color: Nearest RHS 137B;

Axillary branches: Three to six, rarely two per main stem; between 6.0 to 12.0 cm long and 4.0 to 6.0 mm diameter; at angles of about 30° from main stem;

Axillary branch color: Nearest RHS 137B;

Leaves: Lanceolate to linear; apex acute; base attenuate; alternate; sparsely puberulent; margin serrate and ciliolate with about eight teeth per side, and size about 1.0 mm long and 1.0 mm wide; adaxial and abaxial nearly microscopically; lowest leaves about 12.0 cm long and 1.7 cm wide, average about 10.0 cm long and 1.4.1 cm wide; no fragrance detected;

Leaf color: Adaxial color nearest RHS 137B, abaxial color between RHS 137C and RHS 138A;

Veins: Anastomosing, adaxial slightly raised, abaxial midrib costate and secondary veins smooth;

Vein color: Adaxial midrib nearest RHS 146D, secondary veins nearest RHS 147C; abaxial midrib nearest RHS 146D and secondary veins between RHS 137C and RHS 138A;

Inflorescence: Capitate, about 140 per plant at one time; primary inflorescence 9.0 cm across and 5.0 cm tall; comprising about 3 to 4 outer rows of larger ray florets, 3 to 5 rows of smaller ray florets and about 200 to 300 disk florets; individual inflorescence lasting about three weeks on or cut from plant;

Fragrance: No fragrance detected;

Flowering period: Early summer (late June) to early autumn in Michigan if deadheaded;

Peduncle: Strong, stiff; hispidulous to puberulent; round and longitudinal costate; 6.0 to 12.0 cm long and about 4.0 mm diameter at base; upwardly;

Peduncle color: Nearest RHS 137B;

Bud: With ray florets still vertical, 2.7 cm across ray florets and 2.5 cm from base of phyllaries to apex of capitulum;

Bud color: Adaxial and abaxial ray floret coloration between RHS 1C and RHS 2B;

Larger outer ray florets: About 135 per inflorescence; arranged around perimeter of capitulum in 3 to 4 overlapping rows; glabrous adaxial and abaxial; to 40.0 mm long and 10.0 mm wide, cleft types with lobes apices variably spreading to about 25.0 mm wide; lanceolate to linear; emarginate to 1.0 mm deep at apex with three lobes cleft to 20.0 mm deep; base attenuate, margin entire; longitudinal axis reflexing, flat and slightly twisted;

Smaller inner ray florets: About 130 per inflorescence; arranged inside larger ray florets in 3 to 5 rows; glabrous adaxial and abaxial; to about 25.0 mm long, 8.0 mm wide and lobe apices spreading to about 10.0 mm wide; linear; apex cleft with 3 to 4 lobes cleft to about 14.0 mm deep; base attenuate; margin entire; longitudinal axis straight when young, becoming incurving and twisted with maturity;

Disk florets: To about 300 per inflorescence in center of capitulum, combined florets about 18.0 mm across and about 12.0 mm tall; individual floret about 6.0 mm tall and 1.2 mm wide, five tepals, about 3.0 mm long; with acute apex, fused in basal 2.0 mm;

Outer ray floret color: As florets are first at 180° horizontal adaxial and abaxial nearest RHS 4D with base nearest RHS 145A; mature floret adaxial between RHS NN155D and RHS NN155C and abaxial nearest RHS NN155C with base nearest RHS 145A;

Inner ray floret color: As florets are first expanding adaxial and abaxial nearest RHS 4B with base nearest RHS 146D; mature floret adaxial nearest RHS 146D;

Disk floret color: Adaxial and abaxial tepal nearest RHS 9A distally and nearest RHS 8B proximally;

Androecium: Five stamens connate around style; in disk florets only;

*Anther*.—Five; connate into tube; about 2.0 mm long and less than one mm wide, rudimentary in ray florets, functional in disk florets; coloration nearest RHS N200A.

*Filaments fused together at apex, about* 2.0 *mm long and less than* 0.1 *mm diameter, filament coloration nearest RHS NN*155C.

*Pollen*.—Only found in disk florets.

Gynoecium: In ray florets and disk florets; to about 7.0 mm long;

*Style*.—About 5.0 mm long and less than 0.5 mm diameter, split and curved at apical 1.0 mm; color nearest RHS 145C.

*Stigma less than* 0.5 *mm diameter; color nearest RHS* 9B.

Involucre: Made of about three layers of phyllaries; to 4.0 cm across and 0.6 cm tall;

Phyllaries: Lanceolate; glabrous; margin entire and transparent; apex acute; base truncate; to about 60 per head arranged in about three overlapping rows, 9.0 mm long and 4.0 mm wide;

Phyllaries color: Adaxial center nearest RHS NN137C, margin transparent, region between margin and center nearest RHS N199B; abaxial center portions nearest RHS 137B, margin transparent, region between center and margin nearest RHS N199B;

Fruit: Achene, pointed at base and rounded at distal end with longitudinal color striations nearest RHS N200A and lighter than RHS 155D; about 3 to 4 mm long and 1.5 mm across;

Leucanthemum 'Ice Cream Dream' grows best with adequate moisture but can tolerate some dryness once established. It is tolerant of high temperatures of at least 36° C. and cold hardy to at least USDA zone 5 as well as strong wind and rain. Other disease or pest resistance beyond that common to Shasta daisy has not been observed.

I claim:

1. The new and distinct Shasta daisy plant *Leucanthemum* 'Ice Cream Dream' as herein shown and described.

* * * * *